United States Patent
Wehner et al.

(10) Patent No.: US 6,489,131 B1
(45) Date of Patent: Dec. 3, 2002

(54) INTERFERENCE REDUCTION BY RHEUMATOID FACTORS

(75) Inventors: Rainer Wehner, Tutzing (DE); Frederic Donie, Tutzing (DE); Beatus Ofenloch-Hähnle, Polling (DE)

(73) Assignee: Roche Diagnostics GmbH, Mannheim (DE)

(*) Notice: Subject to any disclaimer, the term of this patent is extended or adjusted under 35 U.S.C. 154(b) by 0 days.

(21) Appl. No.: 09/306,600

(22) Filed: May 6, 1999

(30) Foreign Application Priority Data

May 6, 1998 (DE) ......................... 198 20 239
Mar. 23, 1999 (DE) ......................... 199 13 117

(51) Int. Cl.$^7$ ..................... G01N 33/546; G01N 33/53; G01N 33/543; C12Q 1/00
(52) U.S. Cl. ..................... 435/7.92; 435/4; 435/5; 435/6; 435/7; 435/7.1; 435/7.2; 435/7.21; 435/7.5; 435/7.8; 435/7.92; 435/7.93; 435/7.94; 435/172.1; 435/188; 435/184; 435/810; 435/962; 435/974; 435/975; 436/501; 436/518; 436/536; 436/537; 436/543; 436/546; 436/73; 436/172; 436/175; 436/824; 436/825; 436/820; 436/534; 424/8; 424/12; 530/300; 530/324; 530/325; 530/326; 530/327; 530/333; 530/334; 530/402; 530/807
(58) Field of Search ......................... 435/4, 5, 6, 7, 435/7.2, 7.1, 721, 7.5, 7.8, 7.92, 7.93, 7.94, 975, 962, 172.1, 188, 184, 810, 974; 436/501, 518, 536, 537, 543, 546, 73, 172, 175, 824, 825, 820; 424/8, 12; 530/300, 324, 325, 326, 327, 333, 334, 402, 807

(56) References Cited

U.S. PATENT DOCUMENTS

| | | | |
|---|---|---|---|
| 4,281,061 A | * 7/1979 | Zuk et al. | 435/7 |
| 4,595,661 A | 6/1986 | Cragle et al. | 436/534 |
| 4,743,542 A | 5/1988 | Graham, Jr. et al. | 435/7 |
| 4,745,076 A | 5/1988 | Muller | 436/537 |
| 4,945,042 A | 7/1990 | Geiger | 435/7 |
| 5,258,503 A | * 11/1993 | Yokohari et al. | 530/415 |
| 5,358,852 A | 10/1994 | Wu | 435/7.94 |
| 5,466,611 A | 11/1995 | Toth | 436/534 |
| 5,804,371 A | * 6/1996 | Hoss et al. | 435/5 |
| 5,863,740 A | * 9/1996 | Kientsch-Engel et al. | 435/7.5 |
| 5,759,863 A | 6/1998 | Baumann et al. | 436/507 |
| 5,804,391 A | 9/1998 | Klemt et al. | 435/7.1 |
| 5,914,243 A | 6/1999 | Brust | 435/7.92 |
| 5,965,378 A | 10/1999 | Schlieper et al. | 435/7.9 |
| 5,981,286 A | 11/1999 | Herrmann et al. | 436/84 |

FOREIGN PATENT DOCUMENTS

| | | | | |
|---|---|---|---|---|
| CA | 1336063 | | 11/1988 | ......... G01N/33/576 |
| DE | 198 20 239.3 | * | 5/1998 | ......... G01N/33/543 |
| EP | 0 163 312 | | 12/1985 | ......... G01N/33/53 |
| EP | 0 255 534 | | 4/1992 | ......... G01N/33/533 |
| EP | 0 483 512 A1 | | 5/1992 | |
| EP | 0 580 979 | | 2/1994 | ......... G01N/33/52 |
| EP | 0 617 285 | | 9/1994 | ......... G01N/33/543 |
| EP | 0 617 285 A2 | | 9/1994 | |
| EP | 0809111 | * | 11/1997 | ......... G01N/33/58 |
| EP | 0 809 111 A2 | | 11/1997 | |
| WO | WO 85/02258 | | 5/1985 | ......... G01N/33/53 |
| WO | WO90/05301 | | 5/1990 | ......... G01N/33/50 |
| WO | WO 93/20445 | * | 10/1993 | ......... G01N/33/563 |
| WO | WO 97/07401 | * | 2/1997 | ......... G01N/33/569 |

OTHER PUBLICATIONS

Gilead et al., "An improved technique for the isolation and analysis of immune complexes.," Journal of Immunological Methods, vol. 42, 1981, pp. 67–77.*

Matsushita et al., "establishment and evaluation of a new chemi;uminescent enzyme immunoassay for carcinoembryonic antigen adapted to the fully automated ACCESS system.", European Journal of Clinical Chemistry and Clinical Biochemistry, 1996, vol. 34, page.*

Martins et al., "An evaluation of the effectivenss of three immunoglobulin G (IgG) removal procedures for routine IgM serological testing"., Clinical and Diagnostic Laboratory Immunology, Jan. 1995, pp. 98–103.*

Hoffman et al., Elimination of "Hook–Effect" in two–site immunoradiometric assays by kinetic rate analysis. Clinical Chemistry, vol. 30., No. 9., pp. 1499–1501, 1984.*

Hoffmann et al., "Elimination of Hook–Effect in Two–Site Immunoradiometric Assays by Kinetic Rate Analysis", Clin. Chem. 30 (1984). 1499–1501.

Henle et al., "Rheumatoid factor as a cause of positive reactions n tests for Epstein–Barr virus–specific IgM antibodies", Clin. Ex. Immunol. 36, (1979)36, 415–422.

Ho et al., "Rapid Diagnosis of Acute Epstein–Barr Virus Infection by an Indirect Enzyme–Linked Immunosorbent Assay for Specific Immunoglobulin M (IgM) Antibody without Rheumatoid Factor and Specific IgG Interference", J. Clin. Microbiol. 27 (1989), 952–958.

Thorfason and Diderholm, "False RIA IgM Titres to Herpes Simplex Virus and Cytomegalovirus: Factors Causing Them, and Their Absorption by Protein A–Sepharose/IgG–Protein A–Sepharose", J.Meth.Virol. (1982), 157–170.

Espersen et al., "ELISA Estimations of Rheumatoid Factor IgM, IgA, and IgG in Sera from RA Patients with High Disease Activity, DTT Treatment Studies", Scand. J. Rheumatology, 75(1988), 40–45.

* cited by examiner

Primary Examiner—Christopher L. Chin
Assistant Examiner—Lisa V Cook
(74) Attorney, Agent, or Firm—Marilyn L. Amick; Jill L. Woodburn

(57) ABSTRACT

The invention concerns a method for the determination of an analyte in which rheumatoid factors or rheumatoid-factor-like substances are added as an interference reducing reagent to reduce of avoid a hook effect. The invention in addition concerns suitable reagent kits for carrying out the method.

20 Claims, 2 Drawing Sheets

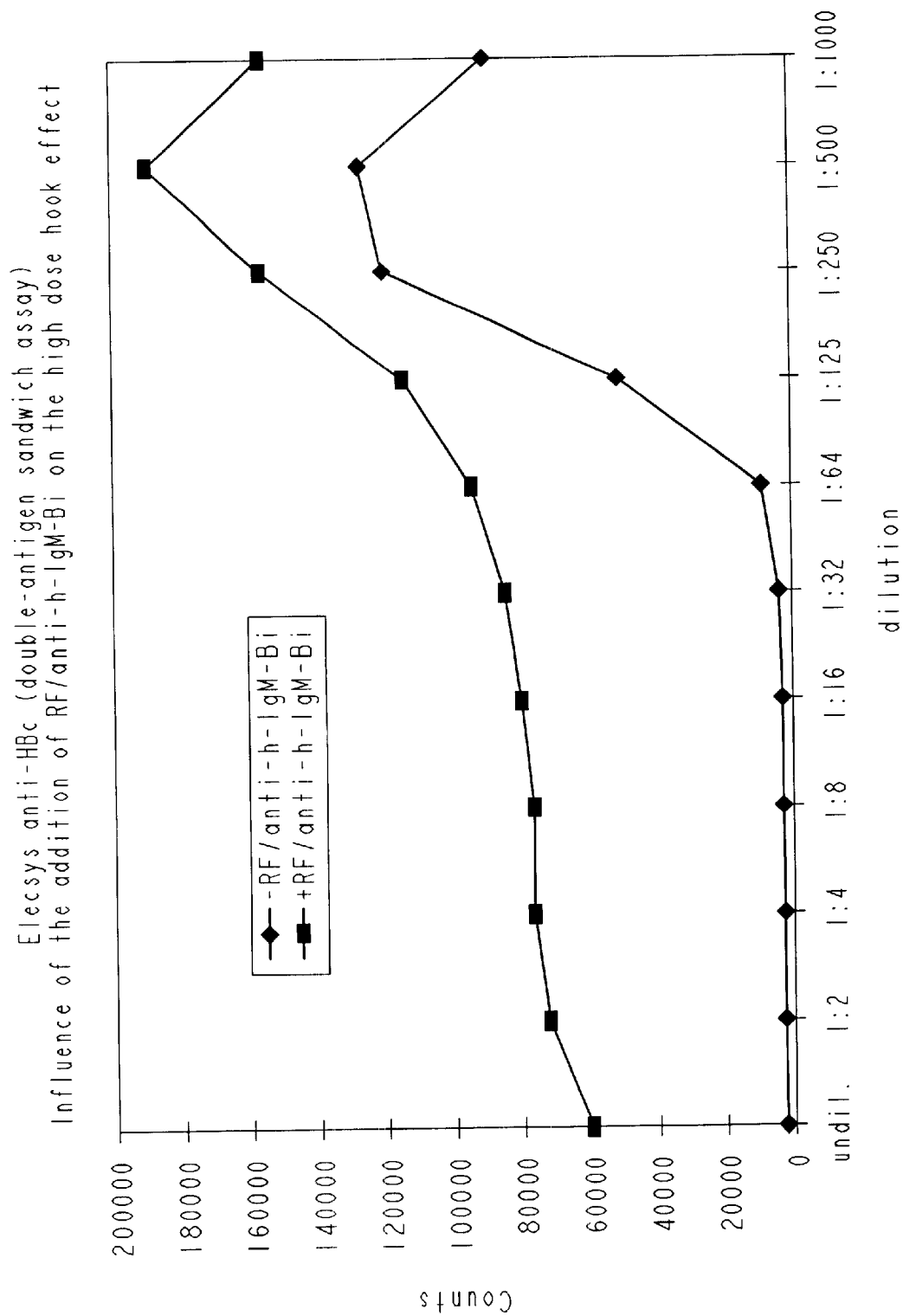

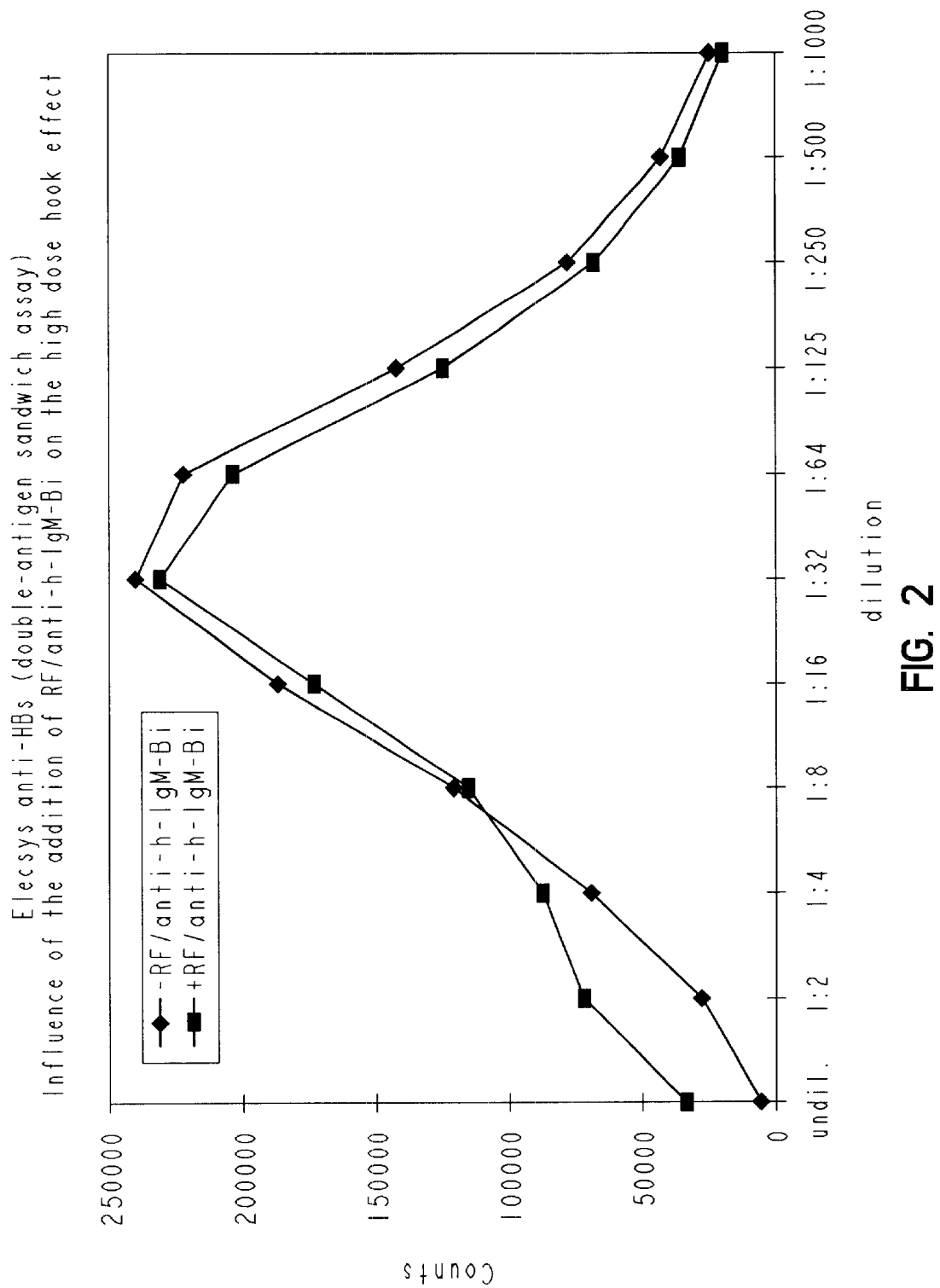

INTERFERENCE REDUCTION BY RHEUMATOID FACTORS

CROSS-REFERENCE TO RELATED APPLICATIONS

This application claims priority under 35 U.S.C. § 119 of German Application Ser. No. 198 20 239.3 filed May 6, 1998 and of German Application Serial No. 199 13 117.1 filed Mar. 23, 1999.

DESCRIPTION

The invention concerns a method for the determination of an analyte in which rheumatoid factors of rheumatoid-factor-like substances are added as an interference reducing reagent to reduce or avoid a hook effect. The invention in addition concerns suitable reagent kits for carrying out the method.

So-called sandwich assays in which two receptors directed against identical or different epitopes of the analyte are incubated with a sample containing the analyte to be determined, are frequently used for the quantitative determination of analytes in a sample. In this method a first soluble receptor is preferably directly or indirectly coupled with a signal-generating system i.e. with a label, whereas—in a heterogeneous detection method—a second receptor is present coupled to a solid phase or is provided with a binding component such as e.g. biotin which is able to bind to a suitably coated solid phase.

The analyte concentration in the sample can vary considerably for a number of diagnostically important parameters which means that a broader measuring range is desirable or even necessary. When such analytes are determined it is, on the one hand, diagnostically important to obtain a value in high concentration ranges which is as accurate as possible. On the other hand, it must also be possible to carry out an exact determination in low concentration ranges to enable a qualitatively correct yes/no diagnosis which in turn can have fundamental therapeutic consequences.

A problem with high analyte concentrations in a sample to be examined is the so-called "high dose hook effect" which is understood as a decrease of the measured signal at very high analyte concentrations. In this case a particular measured signal can be caused by two different analyte concentrations. This "hook effect" considerably limits the application of sandwich assays.

The occurrence of the hook effect is particularly serious in one-step sandwich assays. All tests are referred to as a one-step assay in which the analyte to be determined is reacted with at least two receptors that are specific for it i.e. form a sandwich with it in the same solution and in this process it is for example detected by immobilization on a solid phase in contrast to a sequential reaction procedure in which, after reaction of the analyte with a first specific receptor and immobilization of the complex that is formed on a solid phase, the non-bound analyte is removed by washing the solid phase before the reaction with a second specific labelled receptor.

Sandwich assays can also be carried out to detect antibodies, for example as bridge tests, in which an immobilized or immobilizable antigen that is specific for the antibody to be detected and a second labelled antigen are used. Such bridge test or double-antigen sandwich determinations are described for example in EP-A-0 280 211.

Analyte determinations utilizing the DSAP (double antibody solid phase) sandwich principle in which the two analyte-specific receptors are soluble and the complex with the analyte is immobilized on a solid phase using an additional receptor, are also one-step tests in the above sense and exhibit a hook effect.

Numerous attempts have been made to detect or avoid the hook effect e.g. by carrying out the assay in a two-step or multiple step method in which a wash is carried out after the first reaction step (Hoffmann et al., Clin. Chem. 30 (1984), 1499). However, a disadvantage of this method is that it involves more work, the total incubation time is increased end furthermore there is often a loss of sensitivity and it may not be possible to completely reduce the hook effect.

Another proposal was to carry out several determinations on a single sample with different dilutions in each case. However, this method also increases the amount of time and work that is needed and leads to increased costs for the user.

Hoffmann et al. (1984) supra additionally describe a method of determination for a one-step sandwich test in which the reaction of the analyte with the receptor is monitored kinetically and the values are stored in a computer. This enables measurement results which are caused by the hook effect to be distinguished from other values. A disadvantage of this method is that it requires extremely complicated and expansive computer analyses in order to recognize whether a hook effect is present in the determination.

Other proposals which have been made to reduce or avoid the hook effect also result in considerable disadvantages. Thus a reduction of the sample volume generally leads to a considerable loss of sensitivity. An increase of the receptor concentration (solid phase binding receptor or/and labelled receptor) often leads to a considerable increase in costs and, if the concentration of the labelled receptor is increased, to blank value problems and thus to a loss of sensitivity. Furthermore an increase of the receptor concentration only has a relatively low potential for reducing the hook effect.

Furthermore the addition of unlabelled antibodies or antigens to the test reagent was for example proposed in U.S. Pat. No. 4,595,661, U.S. Pat. No. 4,743,542 or EP-A-0 617 285. However, this also usually leads to a loss of sensitivity and to a considerable increase in the reagent costs.

EP-A-0 572 845 discloses a method for the immunochemical determination of an analyte in a sample by means of a first specific binding partner in which the specific binding partner is immobilized on a carrier and the extent of binding of the analyte to the specific binding partner is determined using an additional specific binding partner which directly or indirectly carries a label and in which a binding factor is additionally added in the method which has more than one site that is capable of binding to the analyte, has no affinity for the immobilized specific binding partner and is not labelled. Examples of such binding factors are monoclonal and polyclonal antibodies as well as fragments thereof, lectins or conjugates of several lectins or conjugates of lectins with analyte-specific antibodies or fragments thereof. When the analyte is an antibody, the antibodies used as binding factors are not homologous to the analyte antibodies and are directed against the specific immunoglobulin class of the analyte antibody. The use of rheumatoid factors to determine human antibodies is neither disclosed nor made obvious.

According to EP-A-0 572 845 the formation of an immune complex is independent of whether the binding faster is present or not. Furthermore it is emphasised that, due to the back reaction known to a person skilled in the art, the complex of analyte and specific receptor can disintegrate again and thus be unavailable for the detection reaction which severely limits the sensitivity. For this reason the diagnostic performance of the test is limited if the back reaction rate between the immobilized receptor and the analyte to be detected is very high. Such a back reaction rate is of particular importance in the lower measuring range i.e. at low concentrations of the analyte or in the case of low affinity anti-analyte antibodies.

Hence the object of the present invention was to at least largely avoid the above-mentioned disadvantages of the prior art. This object is achieved by adding polyclonal or/and monoclonal rheumatoid factors or rheumatoid-factor-like substances to the test mixture as interference reducing reagents. In this manner it is possible to reduce or completely avoid false measurements caused by the hook effect without involving additional time and work and without loss of sensitivity.

Hence a subject matter of the present invention is a method for the determination of an analyte in a sample which is characterized in that rheumatoid factors or rheumatoid factor-like substances are added to reduce interference. The determination is preferably carried out by a sandwich assay, in particular by a one-step sandwich assay. In addition it is preferred that the determination is carried out by a heterogeneous detection method i.e. by means of a solid phase binding of the analyte.

In the method according to the invention the avoidance of false-negative test results due to the hook effect is of primary importance. A possible high back reaction rate in the complex of solid phase-bound analyte and anti-analyte antibody is unimportant since, by definition, a very high analyte concentration is present in the hook effect and thus the back reaction rate is uncritical.

Rheumatoid factors are autoantibodies which are directed against endogenous immunoglobulin, for example IgG. Rheumatoid factors are usually antibodies of the IgM class. Human rheumatoid factors are particularly preferred. Rheumatoid factors have often been described in the literature as interfering substances for immunological methods of detection (cf. e.g, EP-A-0 163 312; Henle et al., Clin. Exp. Immunol. 36 (1979), 415–422; Ho et al., J.Clin. Microbiol. 27 (1989), 952–958; Thorfason and Diderholm, J. Meth. Virol. (1982), 157–170; Espersen et al., Scand. J. Rheumatology, 75 (1988), 40–45; EP-A-0 292 810; DE-OS 42 02 923; PCT/EP95/04307 and PCT/EP95/04308). In view of this prior art it was extremely surprising that the addition of rheumatoid factors can lead to a reduction or even to an elimination of the hook effect.

In addition to rheumatoid factors it is also possible to use rheumatoid-factor-like substances i.e. interference reducing reagents which have the same or similar properties to rheumatoid factors. In particular rheumatoid-factor-like substances can bind oligomeric or polymeric or cross-linked immunoglobulins or immunoglobulins bound to the analyte better than immunoglobulins in a monomeric form. In this connection rheumatoid-factor-like substances are understood as binding factors which have more than one binding site with bioaffinity for the detection antibody. Specific examples of such rheumatoid-factor-like substances are human IgG binding peptides such as peptide fragments of Clq which are described in the U.S. Pat. No. 5,759,863 or monoclonal IgM antibodies which can distinguish between oligomeric human IgG and monomeric human IgG. Such antibodies be obtained by immunizing experimental animals with cross-linked human IgG and isolating monoclonal IgM antibodies with high affinity for oligomeric human IgG and low affinity for monomeric human IgG.

The sample in which the analyte to be determined is present is preferably a biological sample e.g, a sample derived from a body fluid such as blood, serum, plasma, urine, saliva, sperm or cerebrospinal fluid or a tissue or cell culture sample. The sample is preferably a blood, serum or plasma sample and in particular a human sample.

The method according to the invention is preferably carried out as a heterogeneous sandwich assay and comprises the steps:

(a) contacting the sample with a solid phase, a first analyte-specific receptor which is bound to the solid phase or is capable of binding to the solid phase, and a second analyte-specific receptor which carries a signal-generating group or is capable of binding to a signal-generating group and (b) detecting the presence or/and amount of the analyte by determining the signal-generating group on the solid phase.

In addition the method according to the invention preferably comprises an immunological reaction i.e. an antigen-antibody interaction which is used directly or indirectly to determine the analyte. However, the method according to the invention can in principle also be used for other determination reactions which are based on a high affinity interaction and in which there is a risk of the occurrence of a hook effect.

The analyte to be determined can be any substance present in a biological sample, for example an antibody present in a body fluid and in particular an autoantibody, a tumour antibody or an antibody directed against a pathogen e.g. a virus such as HIV or hepatitis viruses. On the other hand the analyte can also be an antigen i.e. a substance that can bind to an antibody for example a tumour marker such as α-fetoprotein or carcinoembryonic antigen or a pregnancy marker such as human chorionic gonadotropin.

The reduction of interference according to the invention by rheumatoid factors or rheumatoid-factor-like substances is preferably used in the determination of antibodies and in particular of human antibodies. In this connection a determination by the previously described bridge test method is particularly preferred.

The so-called indirect method for the detection of antibodies in which a specific antigen for the antibody to be determined is used in an immobilized or immobilizable form and the binding of the analyte antibody is detected by means of a directly or indirectly labelled antibody directed against the analyte antibody is also preferred.

Provided the detection method is not carried out as a turbidimetric or nephelometric test, a signal-generating group is usually used to detect the analyte which can be selected from labels known in the prior art. Examples are radiolabels, enzymes, dyes, fluorescent groups and electrochemiluminescent groups. Electrochemiluminescent groups are particularly preferred e.g. luminescent metal chelate marker groups such as ruthenium chelates e.g. ruthenium-(bipyridiyl)-3-complexes which are described in EP-A-0 178 450, EP-A-0 255 534, EP-A-0 580 979 and WO90/05301. The signal-generating group can either be bound directly to an analyte-specific receptor (direct label) or to a further receptor which is able to bind to the analyte-specific receptor (indirect label).

Solid phases which can be used for the method according to the invention are for example particulate media and especially microbeads such as latex particles and particularly preferably magnetic microbeads or surfaces of reaction vessels, in particular microtitre plates, cuvettes, test tubes, chips and sensors.

When a solid phase is used in a heterogeneous detection method, the test reagent contains a solid-phase analyte-specific receptor. This solid phase receptor can be bound to the solid phase already before the test, for example by adsorptive or covalent interactions but preferably by specific high affinity interactions e.g. striptavidin or avidin/biotin or antibody/antigen interactions. On the other hand, the solid phase receptor can also be present in a form which is capable of binding to the solid phase i.e. it is only bound to the solid phase during the assay and preferably by means of a high affinity interaction. It is particularly preferable to use solid phase) coated with streptavidin or avidin and biotinylated solid phase analyte-specific receptors. In this connection it should be noted that the solid phase receptors can be bound directly as well as indirectly to the solid phase via one or several additional receptors.

In the method according to the invention the rheumatoid factors or rheumatoid-factor-like substances are added to the test mixture in an amount which is adequate on the one hand to reduce interference as extensively as possible i.e. to reduce the hook effect and, on the other hand, not to substantially impair the detection reaction. For this purpose rheumatoid factors can be preferably used in such an amount that they are present at a final concentration of 1 to 1000 U/ml (according to WHO standard 64/2) in the test mixture. Even very small concentrations of rheumatoid factor or rheumatoid-factor-like substances can be effective depending on the extent of the interference reduction. The maximum concentration that can be used is determined by the solubility of the rheumatoid factor or of the other interference reducing substances.

In the method according to the invention the rheumatoid factors can be used in the form of polyclonal or/and monoclonal antibodies, in a purified form or in the form of serum, plasma or fractions thereof. Optionally it is also possible to use antibody fragments In a first embodiment of the method according to the invention the rheumatoid factors or rheumatoid-factor-like substances are added directly to the test mixture in a soluble form. In a further embodiment the rheumatoid factors or rheumatoid-factor-like substances are used in a form bound to a solid phase or in a form that is capable of binding to a solid phase corresponding to the solid phase analyte-specific receptor. Thus for example when using solid phases coated with streptavidin or avidin it is possible to use biotinylated rheumatoid factors. In yet a further embodiment a specific solid phase receptor is used for rheumatoid factors or rheumatoid factor-like substances i.e. a receptor that can bind specifically to the interference reducing reagents and is itself bound to the solid phase or is capable of binding to the solid phase. An anti-IgM antibody e.g. an anti-human IgM antibody can for example be used as the rheumatoid-factor-specific receptor. In this embodiment it is also preferable to use solid phases coated with streptavidin or avidin and biotinylated rheumatoid-factor-specific receptors or biotinylated rheumatoid-factor-like substances or biotinylated receptors therefor.

A further subject matter of the present invention is the use of rheumatoid factors or rheumatoid-factor-like substances as interference reducing reagents in a detection method, in particular in a diagnostic detection method for the determination of an analyte in a biological sample e.g. a body fluid. Rheumatoid factors or rheumatoid-factor-like substances are preferably used to reduce or to avoid the hook effect especially in an immunological method.

Yet a further subject matter of the invention is a reagent kit for the determination of an analyte which, in addition to other reagents, contains rheumatoid factors or rheumatoid-factor-like substances as an interference reducing reagent. The reagent kit preferably additionally contains a solid phase, a first analyte-specific receptor which is bound to the solid phase or is capable of binding to the solid phase and a second analyte-specific receptor which carries a signal-generating group or is capable of binding to a signal-generating group.

The invention is additionally elucidated in more detail by the following examples and figures.

FIG. 1 shows the dependency of the result of an anti-HBc antibody test at different sample dilutions on the addition of rheumatoid factors, FIG. 2 shows the dependency of the result of an anti-HBs antibody test at different sample dilutions on the addition of rheumatoid factors.

EXAMPLES

1. Detection of Anti-hepatitis B core (HBc) Antibodies by Electrochemiluminescence The test was carried out as a double-antigen sandwich assay and is based on the use of a biotinylated HBc antigen and a HBc antigen labelled with a ruthenium complex with an elcectrochemiluminescence capability.

The antigen can be biotinylated by methods known to a person skilled in the art. Ruthenium-labelled antigens can for example be prepared by the method described in WD 96/03651.

An anti-HBc antibody-positive serum with a content of ca. 10,000 U/ml was measured at different dilution steps with or without the addition of rheumatoid factors and anti-human IgM antibody-biotin conjugates as well as streptavidin(SA)-coated magnetic particles.

The ELECSYS® 2010 instrument (manufacturer Boehringer Mannheim/Hitachi) was used according to the operating instructions using the "test protocol 2" program. The test reagents were used as follows:

volumes: 10 $\mu$l sample, 75 $\mu$l reagent 1, 75 $\mu$l reagent 2, 40 $\mu$l streptavidin beads incubation times: 9 min reagent 1 and reagent 2 with sample, further 9 min with SA beads reagent 1: 100 mM Na phosphate buffer, pH 7.4, bovine serum components, detergent, preservative and biotinylated HBcAg (1400 ng/ml)

reagent 2: 100 mM Na phosphate buffer, pH 7.4, bovine serum components, detergent preservative and ruthenylated HBcAg (700 ng/ml)

Biotinylated and ruthenylated HBcAg are incubated together with the sample for 9 min. After addition of streptavidin-coated beads, the incubation is carried out for a further 9 min before determining the electrochemiluminescence.

In the present example reagent 1 additionally contains 0 or 200 U/ml rheumatoid factor and reagent 2 additionally contains 0 or 700 ng/ml biotinylated monoclonal anti-h-IgM antibody.

The final concentration of the rheumatoid factors in the test mixture is 74 U/ml.

The result of the experiment is shown in FIG. 1 and in the following table 1.

TABLE 1

| Sample dilution | −RF/anti-h-IgM-Bi (counts) | +RF/anti-h-IgM-Bi (counts) |
|---|---|---|
| undiluted | 1287 | 59881 |
| 1:2 | 1503 | 72196 |
| 1:4 | 1662 | 76729 |
| 1:8 | 1716 | 75870 |
| 1:16 | 1794 | 78988 |
| 1:32 | 2371 | 82210 |
| 1:64 | 8453 | 94805 |
| 1:125 | 51329 | 114814 |
| 1:250 | 121566 | 156935 |
| 1:500 | 127260 | 190038 |
| 1:1000 | 89452 | 157607 |

Whereas it is only possible to differentiate between positive and negative in the positive anti-HBc serum at a predilution of 1:64 or more without the addition of rheumatoid factors and biotinylated anti-IgM, a positive result (more than 59000 counts) can already be obtained in the undiluted sample when rheumatoid factors and biotinylated anti-IgM are added.

2. Detection of Anti-hepatitis B Surface (HBs) Antibodies by Electrochemiluminescence This test was also carried out as a double-antigen sandwich assay using a biotinylated HBs antigen and a ruthenium-labelled HBs antigen on an ELECSYS® 2010 instrument with the "test protocol 2" program.

A positive HBs serum with a high titre (ca. 400,000 U/l) was measured at various dilution steps with or without the addition of rheumatoid factors and anti-human-IgM biotin conjugate. The reagents were used as follows:

volumes: 40 µl sample, 65 µl reagent 1, 60 µl reagent 2, 35 µl streptavidin beads incubation times; 9 min reagent 1 and reagent 2 with sample, further 9 min with SA beads reagent 1: 80 mM MES buffer, pH 6.5, bovine serum components, detergent, preservative and biotinylated HBaAg (800 ng/ml)

reagent 2: 80 mM MES buffer, pH 6.5, bovine serum components, detergent, preservative and ruthenylated HBsAg (500 ng/ml)

Biotinylated and ruthenylated HBSAg are incubated together with the sample for 9 min. After addition of streptavidin-coated beads, the incubation is carried out for a further 9 min before determining the electrochemiluminescence.

In the present example reagent 1 additionally contains 0 or 200 U/ml rheumatoid factor and reagent 2 additionally contains 0 or 700 ng/ml biotinylated monoclonal anti-h-IgM antibody.

The final concentration of the rheumatoid factors in the test mixture was 65 U/ml.

The result of the experiment is shown in Table 2 and FIG. 2.

TABLE 2

| Sample dilution | anti-HBs conc. (IU/L) | −RF/anti-h-IgM-Bi (counts) | +RF/anti-h-IgM-Bi (counts) |
|---|---|---|---|
| undiluted | 386000 | 4880 | 31483 |
| 1:2 | 193000 | 30097 | 74587 |
| 1:4 | 96500 | 69192 | 84998 |
| 1:8 | 48250 | 120823 | 116538 |
| 1:16 | 24125 | 185021 | 173833 |
| 1:32 | 12063 | 236592 | 230159 |
| 1:64 | 6021 | 221533 | 203239 |
| 1:125 | 3016 | 147461 | 127618 |
| 1:250 | 1508 | 85302 | 73405 |
| 1:500 | 705 | 46226 | 39386 |
| 1:1000 | 386 | 25662 | 22039 |

The results show that the occurrence of the hook effect can be shifted into a higher concentration range without loss of test sensitivity by the addition of rheumatoid factors and biotinylated anti-IgM. A significant gain of sensitivity is achieved in the undiluted or only slightly diluted samples (1:2 or 1:4) by the addition of rheumatoid factors.

3. Detection of Anti-HIV Antibodies by Electrochemiluminescence

The test was carried out according to the HIV combi test is accordance with the German Patent Application DE 197 27 943.0. This is a combined HIV antigen/antibody test. Biotinylated monoclonal anti-p24-antibody (R1) and various biotinylated HIV antigens (R3 and R5) are used as solid-phase-bound receptors. Ruthenylated monoclonal anti-p24 antibodies (R2) and ruthenylated HIV antigens (R4) and (R6) are used as labelled ruthenylated receptors for the detection:

R1: biotinylated monoclonal anti-p24-IqG antibody

R2: ruthenylated monoclonal anti-p24-IgG antibody

R3: biotinylated gp36, gp41 peptides and polyhaptens corresponding to the peptides used in the ENZYMUN® test anti-HIV1+2+SubO, order No. 1557319, Boehringer Mannheim, Germany R4: ruthenylated gp36, gp41 peptides and polyhaptens; the sequences correspond to the peptides used in the Enzymin test anti-HIV1+2+SubO, Order No. 1557319, Boehringer Mannheim, Germany, however, they are ruthenylated and not labelled with digoxigenin R5: biotinylated RT antigen prepared from RT (reverse transcriptase, order No. 1465333, Boehringer Mannheim, Germany R6: ruthenylated RT antigen prepared from RT, Order No. 1465333, Boehringer Mannheim, Germany Ruthenium-labelled HIV antigens and their preparation are described for example in WO 96/03651. Antigens are biotinylated by methods known to a person skilled in the art. The preparation of polyhaptens is described in WO 96/03652.

Anti-HIV-positive samples with high titres were measured at two dilution steps with or without the addition of rheumatoid factors (concentrations 20, 70, 100 U/ml in reagent 1).

The experiment was carried out on an ELECSYS® 2010 according to the operating instructions and the "test protocol 2" program. The test reagents were used as follows:

volumes: 50 µl sample, 50 µl reagent 1, 50 µl reagent 2, 50 µl streptavidin beads incubation times: 9 min reagent 1 and reagent 2 with sample, further 9 min with beads reagent 2. Tris buffer, pH 8.0, bovine serum components, detergent, preservative and biotinylated antigens or antibodies (R1, R3, R5)

reagent 2: Tris buffer, pH 8.0, bovine serum components, detergent, preservative and ruthenylated antigens or antibodies (R2, R4, R6).

The receptors R1 to R6 (antibodies, polyhaptens and RT: 100–2000 ng/ml in each case, 10–100 ng/ml peptides) in the reagents 1 and 2 are incubated with the sample for 9 min. After addition of streptavidin-coated beads they are incubated for a further 9 min before determining the electrochemiluminescence.

In the present example reagent 1 additionally contains 0, 20, 70 or 200 U/ml rheumatoid factor by addition of the appropriate amount of human serum (rheumatoid serum) (final concentration of the rheumatoid factors in the test mixture 0; 5; 17.5 and 50 U/ml).

The result of the experiment is shown in Table 3.

TABLE 3

| Sample | Dilution | −RF (counts) | +RF (200 U/ml) (counts) | +RF (70 U/ml) (counts) | +RF (20 U/ml) (counts) |
|---|---|---|---|---|---|
| P.540150 | undiluted | 205177 | 455541 | 281270 | 210898 |
|  | 1:10 | 1550251 | 2037537 | 2096947 | 1915043 |
| P.540152 | undiluted | 206720 | 547183 | 337802 | 240242 |
|  | 1:10 | 1470259 | 2035675 | 2080025 | 1850273 |
| P.540153 | undiluted | 320276 | 788653 | 534850 | 385940 |
|  | 1:10 | 1056538 | 1774282 | 1713066 | 1398399 |
| P.540154 | undiluted | 393020 | 602461 | 449528 | 429016 |
|  | 1:10 | 1893222 | 2036687 | 2000572 | 1930526 |
| P.540157 | undiluted | 394565 | 844008 | 612468 | 472606 |
|  | 1:10 | 830366 | 1246561 | 1047513 | 898250 |
| P.540163 | undiluted | 588570 | 1076948 | 813437 | 649690 |
|  | 1:10 | 2600057 | 2494412 | 2679407 | 2669921 |
| P.540164 | undiluted | 508196 | 1105958 | 865578 | 643729 |
|  | 1:10 | 3065838 | 2567367 | 2857985 | 2964123 |
| P.540169 | undiluted | 467091 | 1030999 | 749894 | 587872 |
|  | 1:10 | 2450779 | 2332767 | 2588618 | 2545663 |
| P.540172 | undiluted | 396806 | 640581 | 489276 | 402892 |
|  | 1:10 | 2122146 | 1515011 | 2139364 | 2278851 |

The results show that the presence of rheumatoid factors considerably reduces the hook effect. Whereas a slight effect or even no effect at all is seen in the diluted samples, the measured signal is greatly increased in the undiluted samples and thus the hook effect is considerably weakened.

What is claimed is:

1. A method for the determination of an analyte in a sample according to the principle of a sandwich assay, said method comprising
   providing a test reagent comprising a first analyte-specific receptor which carries a signal-generating group or is formed to bind to a signal-generating group, and a second analyte-specific receptor which is bound to a solid phase or is formed to bind to a solid phase,
   forming a test mixture comprising the sample, the test reagent and a rheumatoid-factor-like substance in an amount of 1–1000 IU/ml, sufficient to reduce false measurements of the analyte caused by a high dose Hook Effect, the rheumatoid-factor-like substance being selected from human IgG binding peptides and monoclonal IgM antibodies which distinguish between oligomeric human IgG and monomeric IgG,
   incubating the test mixture under conditions wherein the analyte binds to the test reagent,
   separating the signal-generating group bound to the analyte from the unbound signal-generating group, and
   measuring a signal generated by the bound signal-generating group as an indication of the analyte present in the sample.

2. The method of claim 1, wherein said sandwich assay is a one-step sandwich assay.

3. The method of claim 1, wherein said method also comprises binding said analyte to a solid phase.

4. The method of claim 1, said method also comprising the steps of:
   (a) contacting said sample with a solid phase, the test reagent further comprising a second analyte-specific receptor which is bound to said solid phase or is formed to bind to said solid phase and
   (b) the measuring step further comprises detecting the presence or/and amount of said analyte by determining said signal-generating group on said solid phase.

5. The method of claim 1, wherein said method comprises an antigen-antibody interaction.

6. The method of claim 1, wherein said analyte is selected from the group consisting of antibodies and antigens.

7. The method of claim 6, wherein said analyte is an antibody and said determination is carried out by a double-antigen bridge test.

8. The method of claim 6, wherein said analyte is an antibody and said determination is carried out by an indirect detection method.

9. The method of claim 1, wherein said analyte is detected using a signal-generating group selected from the group consisting of radiolabels, enzymes, dyes, fluorescent groups and electrochemiluminescent groups.

10. The method of claim 3, wherein said solid phase is selected from the group consisting of microbeads, microtitre plates, cuvettes, test tubes, chips and sensors.

11. The method of claim 4, wherein said solid phase is coated with streptavidin or avidin and a biotinylated first analyte-specific receptor is used.

12. The method of claim 1, wherein said rheumatoid-factor-like substances are present at a final concentration of 1 to 1000 IU/ml test mixture.

13. The method of claim 1, wherein said rheumatoid-factor-like substances are added in a soluble form.

14. The method of claim 1, wherein said rheumatoid-factor-like substances are bound to a solid phase or are formed to bind to a solid phase.

15. The method of claim 4, wherein a specific receptor for said rheumatoid-factor-like substances is additionally used which is bound to a solid phase or are formed to bind to a solid phase.

16. The method of claim 15, wherein said specific receptor for said rheumatoid-factor is an anti-IgM antibody.

17. The method of claim 14, wherein said solid phase is coated with streptavidin or avidin and said rheumatoid-factor-like substance is biotinylated.

18. The method of claim 15, wherein said solid phase is coated with streptavidin or avidin and said receptor specific for rheumatoid-factor-like substances is biotinylated.

19. The method of claim 4, wherein said analyte is selected from the group consisting of anti-HBc, anti-HBs and anti-HIV.

20. The method of claim 1, wherein the rheumatoid-factor-like substance is present at a concentration of 1 to 1000 IU/ml test mixture.

* * * * *